(12) United States Patent
Tomany et al.

(10) Patent No.: US 8,598,522 B2
(45) Date of Patent: Dec. 3, 2013

(54) TECHNIQUES FOR AUTOMATED PARAMETER ADJUSTMENT USING ION SIGNAL INTENSITY FEEDBACK

(75) Inventors: Michael J. Tomany, North Grosvenordale, CT (US); James P. Murphy, Franklin, MA (US); Paul Rainville, Princeton, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/698,336

(22) PCT Filed: May 9, 2011

(86) PCT No.: PCT/US2011/035693
§ 371 (c)(1),
(2), (4) Date: Nov. 16, 2012

(87) PCT Pub. No.: WO2011/146269
PCT Pub. Date: Nov. 24, 2011

(65) Prior Publication Data
US 2013/0056631 A1 Mar. 7, 2013

Related U.S. Application Data

(60) Provisional application No. 61/347,029, filed on May 21, 2010.

(51) Int. Cl.
*G01N 30/72* (2006.01)

(52) U.S. Cl.
USPC ...................................................... 250/288

(58) Field of Classification Search
CPC ......................... G01N 30/724; G01N 30/7246
See application file for complete search history.

(56) References Cited

U.S. PATENT DOCUMENTS

| 3,238,752 A |   | 3/1966 | Dilling |
|---|---|---|---|
| 4,948,962 A | * | 8/1990 | Mitsui et al. .................. 250/288 |
| 5,384,465 A |   | 1/1995 | Armour et al. |
| 5,460,973 A |   | 10/1995 | Schrader |

(Continued)

FOREIGN PATENT DOCUMENTS

JP 04149950 A * 5/1992

OTHER PUBLICATIONS

Covey et al., Atmospheric Pressure Ion Sources, Mass Spectrometry Reviews, 28:870-897, Published Jul. 22, 2009, Wiley Periodicals, Inc.

*Primary Examiner* — Robert Kim
*Assistant Examiner* — James Choi
(74) *Attorney, Agent, or Firm* — Muirhead and Saturnelli, LLC (57) ABSTRACT

Described are techniques for tuning parameters of a system. For one or more values of a distance, mass spectral analysis of a liquid analyte stream is performed. A corresponding ion signal intensity of a selected ion is obtained. The distance is measured from a first end of a first tube to a second end of a second tube which surrounds said first tube. Using a computing device, a current value of the distance is automatically adjusted in accordance with corresponding ion signal intensities obtained for the selected ion. Using a computing device, a desired value for the distance is automatically determined using the corresponding ion signal intensities. The desired value results in an ion signal intensity for the selected ion which is any of more than a threshold intensity and a maximum of ion signal intensities obtained by performing mass spectral analysis using different values for the distance.

19 Claims, 7 Drawing Sheets

(56) References Cited

U.S. PATENT DOCUMENTS

| | | | |
|---|---|---|---|
| 6,166,379 A * | 12/2000 | Montaser et al. | 250/288 |
| 6,294,088 B1 | 9/2001 | Allington et al. | |
| 6,870,154 B1 * | 3/2005 | Konermann et al. | 250/281 |
| 7,122,791 B2 | 10/2006 | Joyce et al. | |
| 7,372,023 B2 | 5/2008 | Sobek et al. | |
| 2003/0052268 A1 | 3/2003 | Doroshenko et al. | |
| 2006/0258017 A1 | 11/2006 | Gullett et al. | |
| 2008/0006769 A1 * | 1/2008 | Staats | 250/288 |
| 2009/0294660 A1 * | 12/2009 | Whitehouse et al. | 250/288 |
| 2010/0133431 A1 * | 6/2010 | Tomany et al. | 250/287 |

* cited by examiner

TECHNIQUES FOR AUTOMATED PARAMETER ADJUSTMENT USING ION SIGNAL INTENSITY FEEDBACK

RELATED APPLICATION

This application is a National Stage of International Application No. PCT/US2011/35693, filed May 9, 2011, which claims priority to U.S. Provisional Application No. 61/347,029, filed May 21, 2010, all of which are incorporated by reference herein.

BACKGROUND

1. Technical Field

This application generally relates to automated parameter adjustment to obtain a desired or maximum ion signal intensity as determined using mass spectrometry, and more particularly to techniques for automatically adjusting parameters using ion signal intensity feedback to obtain optimal parameter settings.

2. Description of Related Art

Samples may be processed in a laboratory or other environment for a variety of different purposes and applications. Chromatography refers to techniques for separating sample mixtures. Common chromatographic techniques include gas chromatography (GC) and liquid chromatography (LC). With an instrument that performs LC, a liquid sample to be analyzed is introduced in small volumes for analysis. The sample may be injected into a solvent stream which is carried through a column. The compounds in the sample can then be separated by traveling at different speeds through the column resulting in the different compounds eluting from the column at different times. In connection with High Performance Liquid Chromatography (HPLC) and Ultra Performance Liquid Chromatography (UPLC), pressure is used to facilitate fluid flow in the system through the chromatographic column.

Mass spectrometry (MS) is used widely for identifying and quantifying molecular species in a sample. During analysis, molecules from the sample are ionized to form ions. A detector produces a signal relating to the mass of the molecule (or cluster of molecules) and charge carried on the molecule (or cluster of molecules) and a mass-to-charge ratio (m/z) for each of the ions is determined.

A chromatographic separation technique, such as LC or GC, may be performed prior to sample analysis using mass spectrometry. When coupled to a mass spectrometer, the resulting systems are referred to as GC/MS or LC/MS systems. GC/MS or LC/MS systems are typically on-line systems in which the output of the GC or LC is coupled directly to the MS.

In an LC/MS system, a sample is injected into the liquid chromatograph at a particular time. The liquid chromatograph causes the sample to elute over time resulting in an eluent that exits the liquid chromatograph. The eluent exiting the liquid chromatograph is continuously introduced into the ionization source of the mass spectrometer. As the separation progresses, the composition of the mass spectrum generated by the MS evolves and reflects the changing composition of the eluent. Typically, at regularly spaced time intervals, a computer-based system samples and records the spectrum. The response (or intensity) of an ion is the height or area of the peak as may be seen in the spectrum. The spectra generated by conventional LC/MS systems may be further analyzed. Mass or mass-to-charge ratio estimates for an ion are derived through examination of a spectrum that contains the ion.

SUMMARY OF THE INVENTION

In accordance with one aspect of the invention is a system. The system includes a tubing arrangement, a positioning apparatus, a mass spectrometer and a computing device. The tubing arrangement includes a first tube surrounded by a second tube, wherein an analyte stream flows through the first tube and exits at a first end thereof. The second tube has a nebulizing gas flowing therethrough that exits the second tube at a second end thereof. At least the second tube is linearly movable with respect to a center axis therethrough. The positioning apparatus is configured to linearly adjust a position of the second end of the second tube relative to the first end of the first tube in response to control signals. The mass spectrometer is configured to output a signal indicating an ion signal intensity for an ion. The computing device is electrically connected to the mass spectrometer and the positioning apparatus. The computing device is configured to receive the signal from the mass spectrometer indicating the ion signal intensity for the ion, to determine, in accordance with the signal, an adjustment to a current position of the second end of the second tube relative to the first end of the first tube, and to send the control signals to the positioning apparatus to linearly adjust a current position of the second tube relative to the first tube in accordance with the adjustment. The computing device may be further configured to repeatedly determine an adjustment to a current position of said second end of said second tube relative to said first end of said first tube, and accordingly send control signals to said positioning apparatus until said ion signal intensity of the ion is determined as acceptable by said computing device. The ion signal intensity may be determined as acceptable if said ion signal intensity is a maximum ion signal intensity for the ion. The ion signal intensity may be determined as acceptable when more than a specified threshold intensity. The positioning apparatus may include a motor, a worm gear and a drive gear. The motor may be coupled to said worm gear and the worm gear may be coupled to said drive gear. The motor may receive control signals from the computing device causing said worm gear to rotate about its center axis. The drive gear may rotate about its center axis in response to rotation of said worm gear about its center axis. The second tube may be threaded and may pass through a center of said drive gear and, in response to the drive gear rotating about its center axis, the second tube may have its position varied linearly. The system may also include one of a pump or a liquid chromatograph coupled to the tubing arrangement and providing the analyte stream. The computing device may determine an amount by which the motor rotates the worm gear.

In accordance with another aspect of the inventions is a method for tuning parameters of a system comprising: performing, for each value in a set of one or more values of a distance, mass spectral analysis of a liquid analyte stream when said distance is set to said each value and obtaining a corresponding ion signal intensity of a selected ion, wherein said distance is measured from a first end of a first tube to a second end of a second tube which surrounds said first tube, said liquid analyte stream flowing through said first tube and exiting at said first end, a nebulizing gas flowing through said second tube and exiting at said second end; automatically adjusting, using a computing device, a current value of said distance in accordance with one or more corresponding ion signal intensities obtained for said selected ion by performing said mass spectral analysis; and automatically determining, using a computing device, a desired value for said distance using corresponding ion signal intensities of said selected ion obtained from performing said mass spectral analysis, wherein said desired value for said distance results in an ion signal intensity for said selected ion which is any of more than a threshold intensity and a maximum of a plurality of ion signal intensities obtained by performing said mass spectral analysis using different values for said distance. The distance may be adjusted by adjusting a position of one or more of said first tube and said second tube using a positioning apparatus controlled by a computing device. The positioning apparatus may include a motor which operates responsive to control signals transmitted by a computing device.

In accordance with another aspect of the invention is a method for tuning parameters of a system comprising: performing, for each value in a set of one or more values of a distance, mass spectral analysis of a liquid analyte stream when said distance is set to said each value and obtaining a corresponding ion signal intensity of a selected ion, wherein said distance is a relative distance between two exit points in a tubing arrangement of a plurality of concentric tubes, said first exit point being a location at which said liquid analyte stream exits said tubing arrangement, said second exit point being a location at which a heated desolvation gas exits said tubing arrangement; automatically adjusting, using a computing device, a current value of said distance in accordance with one or more corresponding ion signal intensities obtained for said selected ion by performing said mass spectral analysis; and automatically determining, using a computing device, a desired value for said distance using corresponding ion signal intensities of said selected ion obtained from performing said mass spectral analysis, wherein said desired value for said distance results in an ion signal intensity for said selected ion which is any of more than a threshold intensity and a maximum of a plurality of ion signal intensities obtained by performing said mass spectral analysis using different values for said distance. The tubing arrangement may include a first tube through which said liquid analyte stream flows and which is surrounded by a second tube through which a nebulizing gas flows. The second tube may be surrounded by a third tube enclosing an air gap. The third tube may be surrounded by a fourth tube. The heated desolvation gas may flow between said third tube and said fourth tube. The distance may be adjusted by adjusting a position of one or more of said first tube, and said third and fourth tubes using a positioning apparatus controlled by a computing device. The positioning apparatus may include a motor which operates responsive to control signals transmitted by a computing device.

In accordance with another aspect of the invention is a method for tuning one or more ion source parameters comprising: selecting an ion; and, for each of said one or more ion source parameters, performing processing including: performing, for each value in a set of one or more values for said each ion source parameter, mass spectral analysis of a liquid analyte stream when said each ion source parameter is set to said each value and obtaining a corresponding ion signal intensity of said ion; automatically adjusting, using a computing device, a current value of said each ion source parameter in accordance with one or more corresponding ion signal intensities for said ion obtained by performing said mass spectral analysis; and automatically determining, using a computing device, a desired value for said each ion source parameter using corresponding ion signal intensities obtained from performing said mass spectral analysis of said ion, wherein said desired value for said each ion source parameter results in an ion signal intensity for said ion which is any of more than a threshold intensity and a maximum of a plurality of ion signal intensities obtained by performing said mass spectral analysis using different values for said each ion source parameter, said one or more ion source parameters including at least one of a first distance measured from a first end of a first tube through which a liquid analyte stream flows and exits at said first end to a second end of a second tube which surrounds said first tube and through which a nebulizing gas flows and exits at said second end, a second distance measured from said first end and a third end of a third tube from which a heated desolvation gas flows, a nebulizer gas pressure, a nebulizer gas flow, a desolvation gas temperature, a desolvation gas flow, and a three-dimensional positioning of an electrospray interface with respect to a mass spectrometer performing the mass spectral analysis, said electrospray interface being an interface at which electrospray ionization occurs. The liquid analyte stream may be injected using an infusion pump when tuning each of said one or more ion source parameters. Once a desired value for each of said one or more ion source parameters is determined, the infusion pump may be replaced with a liquid chromatograph. Once a desired value for a first of said one or more ion source parameters is determined, the first ion source parameter may be set to said desired value when performing subsequent analysis.

BRIEF DESCRIPTION OF THE DRAWINGS

Features and advantages of the present invention will become more apparent from the following detailed description of exemplary embodiments thereof taken in conjunction with the accompanying drawings in which.

DETAILED DESCRIPTION OF EMBODIMENT(S)

Techniques described in following paragraphs may be used in connection with an embodiment of an LC/MS system that performs liquid chromatography (LC) and mass spectrometry (MS). The LC separation technique is performed prior to injecting the sample in a mass spectrometer for analysis. In connection with MS analysis, molecules from the sample are ionized to form ions. A detector produces a signal relating to the mass of the molecule (or cluster of molecules) and charge carried on the molecule (or cluster of molecules) and a mass-to-charge ratio (m/z) for each of the ions is determined. The LC/MS technique produces a variety of observed measurements for every detected ion. These measurements may include the retention time of the ion, the mass-to-charge ratio (m/z) and the signal intensity of the ion, such as a number of ions counted.

Figure 1:
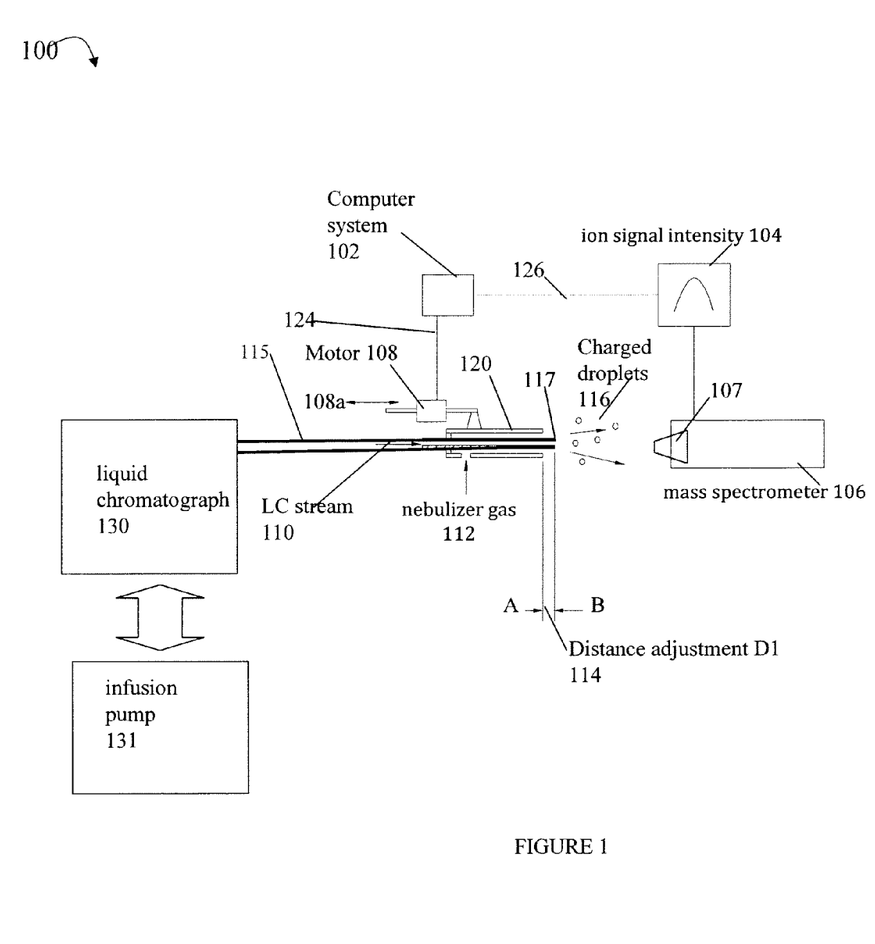
FIG. 1 is an example illustrating components that may be included in an embodiment of a system in accordance with techniques described herein.

Referring to FIG. 1, shown is an example of components of a system in accordance with techniques herein. In the LC/MS system, a sample is injected into the liquid chromatograph 130 at a particular time. The liquid chromatograph 130 causes the sample to elute over time resulting in an eluent that exits the liquid chromatograph 130 as part of the LC stream 110. The eluent exiting the liquid chromatograph 130 is continuously introduced into the system 100 illustrated in FIG. 1. As the separation progresses, the composition of the mass spectrum generated by MS evolves and reflects the changing composition of the eluent. Typically, at regularly spaced time intervals, a computer-based system 102 samples and records the spectrum. The response (or intensity 104) of an ion is the height or area of the peak as may be seen in the spectrum. The techniques herein may be used to perform analysis and processing using the intensity (also referred to as the ion signal intensity 104) for a given ion (having a particular m/z, retention time, and the like as may be used to identify the ion in the spectrum) to tune and adjust one or more parameters of the system as described in more detail in following paragraphs. Mass or mass-to-charge (m/z) ratio estimates for an ion are derived through examination of a spectrum that contains the ion.

In an embodiment of an LC/MS system in accordance with techniques herein, the output of the liquid chromatograph 130 is coupled to, or interfaced with, the mass spectrometer 106 through an electrospray interface. Prior to performing mass spectrometry by 106, the eluent of the LC stream 110 output from the LC separation process is subjected to an ionizing process known as electrospray ionization (ESI) causing generation of charged droplets 116. The charged droplets 116 may be generated through application of a voltage to the LC stream alone, or in combination with, a nebulizing gas 112, heated desolvation gas, and the like, depending on the flow rate of the LC stream. A suitable voltage (e.g., 1-5 KV) may be applied to the LC stream 110 such as, for example, via metal tubing containing the LC stream 110. A suitable voltage (e.g., 50V) is also applied at the inlet 107 of the mass spectrometer 106 so that an electrical field exists between the tip portion 117 of the tube from which the LC stream 110 exits and the inlet 107 of the mass spectrometer 106 resulting in charged droplets 116. The droplets form an elongated conical shape, called a "Taylor cone," at the end of the tip portion 117. As known in the art, a Taylor cone refers to the cone observed in an electrospray process from which a jet of charged droplets or particles emanates. When a small volume of electrically conductive liquid that may be provided from the tip portion 117 is exposed to an electric field, the shape of the liquid starts to deform from the shape imparted by surface tension. As the electrical field becomes more prominent, such as by increasing a voltage at or near the end of the tip portion, a jet of liquid is emitted from the Taylor cone formed at the end of the tip portion and is the start of the electrospray process in which ions may be transferred to a gas phase. Through the generation of the electrospray by this process, the charged droplets 116 undergo evaporation and breakup into smaller charged droplets, which lead to the generation of ions for analysis by the mass spectrometer 106. The use of the foregoing electrospray process to generate ions for mass spectral analysis by the mass spectrometer is known to those of ordinary skill in the art.

The distance between the Taylor cone formed at the end of the tip portion 117 and the mass spectrometer 106 may vary, for example, from 0.1 cm-10 cm. Using the electrospray ionization process described, as the liquid stream atomized into droplets, the droplets evaporate creating a plume. As droplets travel from the Taylor cone to inlet 107, the droplets evaporate and form positive and/or negative ions which travel into the inlet 107 and are analyzed by 106. In one embodiment, the inlet 107 may be in the form of a cone and a vacuum may be used to draw the particles inward into 106 for analysis. A high electrical field is needed to perform the ionization of the liquid droplets and the voltages used to create the electric field may be varied in accordance with particulars of an embodiment, such as the distance between the Taylor cone and the inlet 107, to achieve the desired ionization process. It should be noted that although the tip portion 117 is illustrated in FIG. 1 as collinear with the axis of the inlet 107, other orientations of the tip portion 117 relative to the inlet 107 are possible.

The mass spectrometer 106 performs mass spectral analysis and may be implemented using standard components known in the art. For example, as known in the art, commercially available mass spectrometers may include an analyzer that sorts the ions in some way in accordance with the masses of the ions, and a detector that measures the relative intensities of different masses or m/z values.

FIG. 1 illustrates the tubing 115 of the LC stream 110 within or surrounded by one or more other concentric tubings. In particular, FIG. 1 provides a lateral view of the tubing 115 containing the LC stream 110 where the tubing 115 is surrounded by an outer concentric tubing 120 for the nebulizing gas 112. The nebulizing gas 112 flows through the tubing 120 surrounding the LC stream tubing 115 and assists in the formation of droplets 116 when the LC stream has a flow rate, for example, above approximately 1 microliter/min. In one embodiment, the outer tubing 120 (through which the nebulizing gas flows) may be moveable along direction 108a relative to the inner tubing 115 (containing the LC stream). The exemplary system 100 also includes a motor 108 which is electrically coupled to, and controlled by control signals from, the computer system 102. The motor 108, in combination with possibly other connected components such as gears, arms, and the like, may be used to adjust the positioning of the tubing 120 along the two-dimensions indicated by 108a.

Described in following paragraphs are techniques that may be used in connection with automated tuning and adjustment to one or more parameters in the system of FIG. 1 using ion signal intensity feedback to achieve a desired or maximum ion signal intensity. In particular, one such parameter that may be automatically tuned and adjusted using techniques herein is a distance D1 114 representing the distance between B, the end or exit (e.g., 117) of the tubing 115 containing the LC stream 110, and A, the exit or ending of the tubing 120 through which the nebulizing gas 112 flows from. As described in more detail below, an embodiment in accordance with techniques herein may use ion signal intensity feedback to have the computer system 102 automatically determine and send appropriate control signals to the motor 108 causing the motor 108 (and possibly other components connected thereto) to adjust the distance D1. The distance D1 may be adjusted, for example, by appropriately modifying the position of tubing 120 relative to the inner tubing 115 in a linear manner as represented by 108a which represents two-dimensional movement parallel to the center axes of the tubings 115 and 120. The exemplary system 100 also includes a motor 108 which is electrically coupled to, and controlled by control signals from, the computer system 102.

The mass spectrometer 106 may output an ion signal intensity 104 as an electrical signal which may be communicated over connection 126 to a computer system 102. Connection 126 may be an electrical connection facilitating communication of the output signal from the mass spectrometer 106 to the computer system 102. The computer system 102 may have executing code thereon which processes the signals received over 126. The signal received over 126 from the mass spectrometer 106 may indicate the intensity of a detected ion at a particular m/z. The computer system 102 may be programmed to compare the current ion signal intensity for a given ion of interest to one or more previously measured ion signal intensities for the same ion. The computer system 102 may determine whether an adjustment to the current value of D1 is needed (such as by comparing the current measured ion signal intensity to one or more other ion signal intensities for the same ion, where each of the one or more other ions signal intensities is measured when D1 has a particular associated value). If an adjustment to D1 is needed, the computer system 102 may determine an appropriate adjustment type (e.g., increase or decrease) and amount of adjustment to be made to D1. The computer system 102 may issue control signals to the motor 108 over electrical connection 124 causing the motor 108 to adjust the positioning of the nebulizer gas tubing 120 along 108a. The computer system 102 may continue to receive measured ion signal intensity readings 104 from the mass spectrometer 106 and accordingly make any appropriate adjustments to the positioning of tubing 120 along the axis indicated by 108a to achieve a maximum optimal ion signal intensity 104 for a particular ion of interest.

Adjustments to D1 may be performed using any one of a variety of different techniques. For example, an embodiment may make adjustments to D1 in relatively small increments and/or decrements and accordingly determine a corresponding ion signal intensity. For example, the tubing 120 may be positioned at a first relative distance D1 with respect to the LC stream tube 115. A first ion signal intensity for a particular ion (having an associated m/z) may be obtained by the mass spectrometer 106 and communicated to the computer system 102. One or more adjustments to D1 (such as by varying the relative distance from the end of tubing 120 and the end of tubing 115) may be made and, for each such D1 value, a measured ion signal intensity for the particular ion obtained. By performing the foregoing repeated process, a final value for D1 may be automatically determined in order to obtain a desired or a maximum optimal ion signal intensity for the particular ion of interest. Thus, processing described herein may traverse a range of D1 values and select the D1 value yielding the largest or maximum ion signal intensity for a particular ion of interest.

The computer system 102 may instruct the motor 108 to move tubing 120 an amount in a direction along 108a. The computer system 102 may so instruct the motor by issuing control signals thereto such as, for example, in response to the computer system 102 determining that an adjustment to D1 is needed or in connection with traversing one of the range of values described herein. The components of FIG. 1 may provide for repeatedly performing the foregoing steps of determining an ion signal intensity measurement for a given ion by the mass spectrometer and having the computer system issue commands to the motor making any further desired adjustments to the distance D1 until the computer system 102 determines that the measured ion signal intensity communicated is at a desired maximum (or within acceptable threshold limit(s)). Each such adjustment may result in adjusting the position of the tubing 120 in some manner along the two-dimensional axis as illustrated by 108a. The ending position of the tubing 120 and the final value of D1 (at which the computer system 102 determines that the desired optimal ion signal intensity is obtained for an ion having a given m/z) may vary with aspects of each system, may vary with each ion observed, and the like. As illustrated by 108a, the motor may position the tubing 120 at various positions using motor 108.

The computer system 102 may be any commercially available or proprietary computer system, processor board, ASIC (application specific integrated circuit), or other component which includes a computer processor configured to execute code such as may be stored on a computer readable medium. The processor, when executing the code, may cause the computer system 102 to perform processing steps as described in accordance with techniques herein. As will be appreciated by those skilled in the art, the code may be stored on any type of computer-readable medium having any one of a variety of different forms including volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, (DVD) or other optical storage, magnetic cassettes, magnetic tape, magnetic disk storage or other magnetic storage devices, or any other medium which can be used to store the desired code which can accessed by a computer processor. The computer system, processor board, and the like, may be more generally referred to as a computing device. The computing device may also include, or otherwise be configured to access, a computer readable medium comprising executable code stored thereon which cause a computer processor to perform processing steps as described in accordance with techniques herein.

It should be noted that tubing 115 may more generally be any type of fluid connection, conduit, or capillary such as a tubing made of metal or other suitable material through which the LC fluid stream may flow. The motor 108 and other components used to adjust the position of tubing 120 in accordance with techniques herein may be more generally referred to as components comprising a positioning device or apparatus configured to adjust the tubing 120 to a desired position and thus adjust the distance D1 in accordance with techniques described herein. An embodiment in accordance with techniques herein may use other components than as provided herein for purposes of example and illustration.

The components of FIG. 1 may be characterized as providing a feedback loop regarding the ion signal intensity obtained for an observed ion using a particular value of parameter D1. The feedback loop in such a system as illustrated provides for automatically adjusting and tuning D1, such as by adjusting the position of 120 in a linear manner as represented by 108a, to obtain a desired or maximum ion signal intensity for the observed ion, as may be identified by having a particular m/z and retention time in a spectrum produced by the mass spectrometer 106.

An embodiment may operate in a first mode that may be characterized as a parameter tuning mode for tuning or adjusting the parameter D1. In such an embodiment, an infusion pump 131 may be used to introduce the fluid stream into the system 100. In this case, the infusion pump 131 may output a constant stream of the analyte for which the parameter D1 is being tuned and the ion of interest may be identified in the resulting MS spectrum by an expected m/z for the ion. In this case, once the value for parameter D1 is tuned, the infusion pump 131 may be replaced with a liquid chromatograph 130 and the system may operate with D1 fixed at the desired optimal setting (as determined by the system using the infusion pump 131 when operating in the first mode).

Once an optimal setting for D1 has been determined, the system may proceed to operate using an LC with D1 fixed at this optimal setting thereby having the tubing arrangement (e.g., position of the LC stream tube with respect to the nebulizing gas tube) remain stationary.

As an alternative to the foregoing embodiment using an infusion pump 131 when tuning the parameter D1, an embodiment may use a liquid chromatograph 130 having a fluid stream flowing therefrom when tuning D1. In this case, the tuning of parameter D1 is performed in a system including a liquid chromatograph rather than an infusion pump to introduce the fluid stream. In this latter embodiment, for a particular compound, an ion of interest may be examined in the resulting MS spectrum in accordance with an expected retention time and m/z value of the ion. Once a tuned value for D1 (e.g., desired or optimal value for D1) has been determined, the system may operate with D1 fixed at this particular value as described above.

Figure 2:
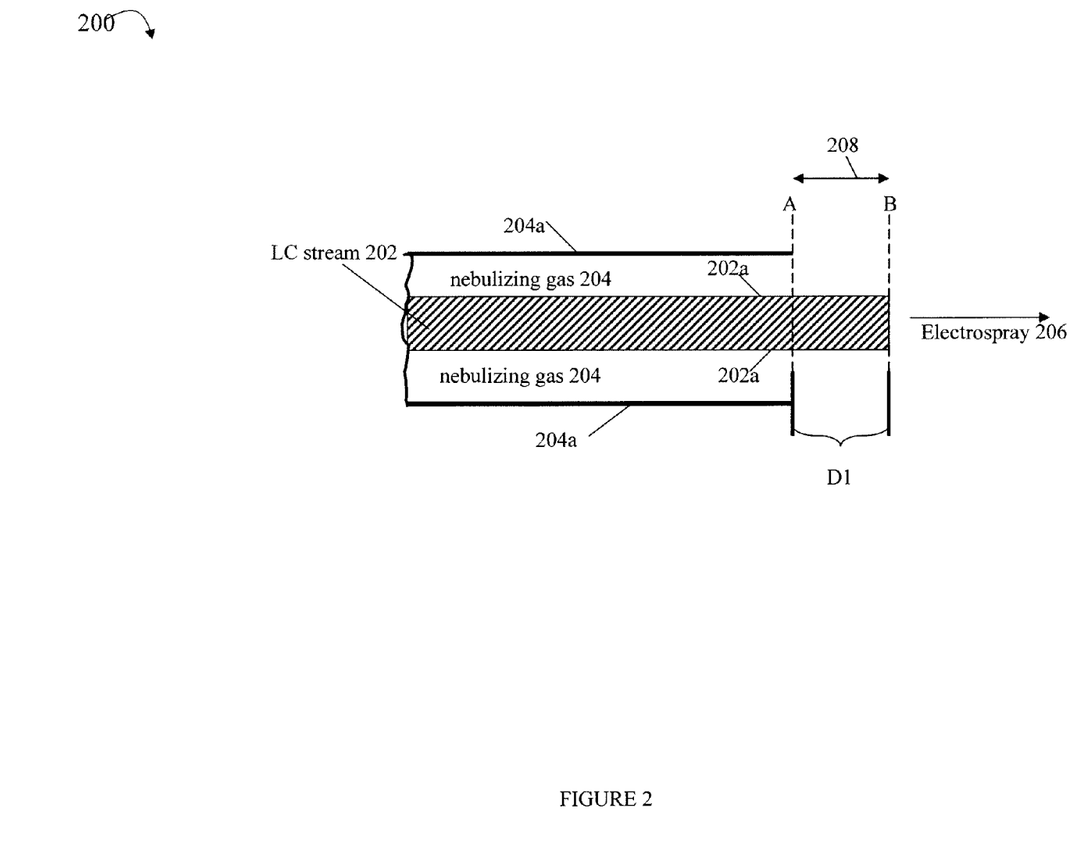
FIG. 2 is an example of a first tubing arrangement that may be used in an embodiment of the system of FIG. 1 in accordance with techniques herein.

Referring to FIG. 2, shown is an example providing additional detail regarding the distance D1 with respect to the components illustrated in the embodiment of FIG. 1. The example 200 provides an enlarged lateral view of the two concentric tubes containing the LC stream and the nebulizing gas at the LC/MS interface where electrospray ionization occurs. The LC stream 202 flows through the inner tube 202a surrounded by an outer concentric tube 204a. The nebulizing gas 204 flows between the walls of the inner tube 202a and the outer concentric tube 204a. In operation, the outer concentric tube 204a may be configured at various horizontal positions as illustrated by 208 (such as using the motor 108 described in connection with FIG. 1) while the inner tube 202a remains stationary. Thus, the distance D1 may be varied. It should be noted that the inner tube 202a protrudes from the outer concentric tube 204a and in connection with adjusting D1 using the techniques herein, the position of A (end of outer tube 204a) is not positioned passed that of B (end of tube 202a). It will be appreciated by those skilled in the art that, although the distance D1 may be adjusted by having tube 202a remain stationary and linearly adjusting tube 204a as described above, the distance D1 may also be varied by having the tube 204a remain stationary and linearly adjusting the position of tube 202a, or linearly adjusting the positions of both tubes 204a and 202a to achieve a desired distance D1.

In one embodiment, the tube 204a may have an inner diameter of approximately 0.012 inches and the outer diameter of the tube 202a may be approximately 0.0065 inches. An example of a nebulizing gas that may be used with the techniques herein is nitrogen at 100 psi (pounds per square inch). An embodiment using the techniques herein may have an LC stream flow rate within the range of, for example, 1 microliter/minute to 200 microliters/minute. It will be appreciated by those skilled in the art that any measurements, operating pressures, and the like, provided herein are approximate and exemplary and may vary with each embodiment. Additionally, systems operating at such exemplary flow rates typically require the use of the nebulizing gas to have suitable droplet formation in connection with the electrospray formation. It should be noted that systems operating at higher flow rates, such as at or above 5 microliters/minutes, may also require use of a heated desolvation gas in addition to the nebulizing gas for sufficient droplet formation.

Figure 3:
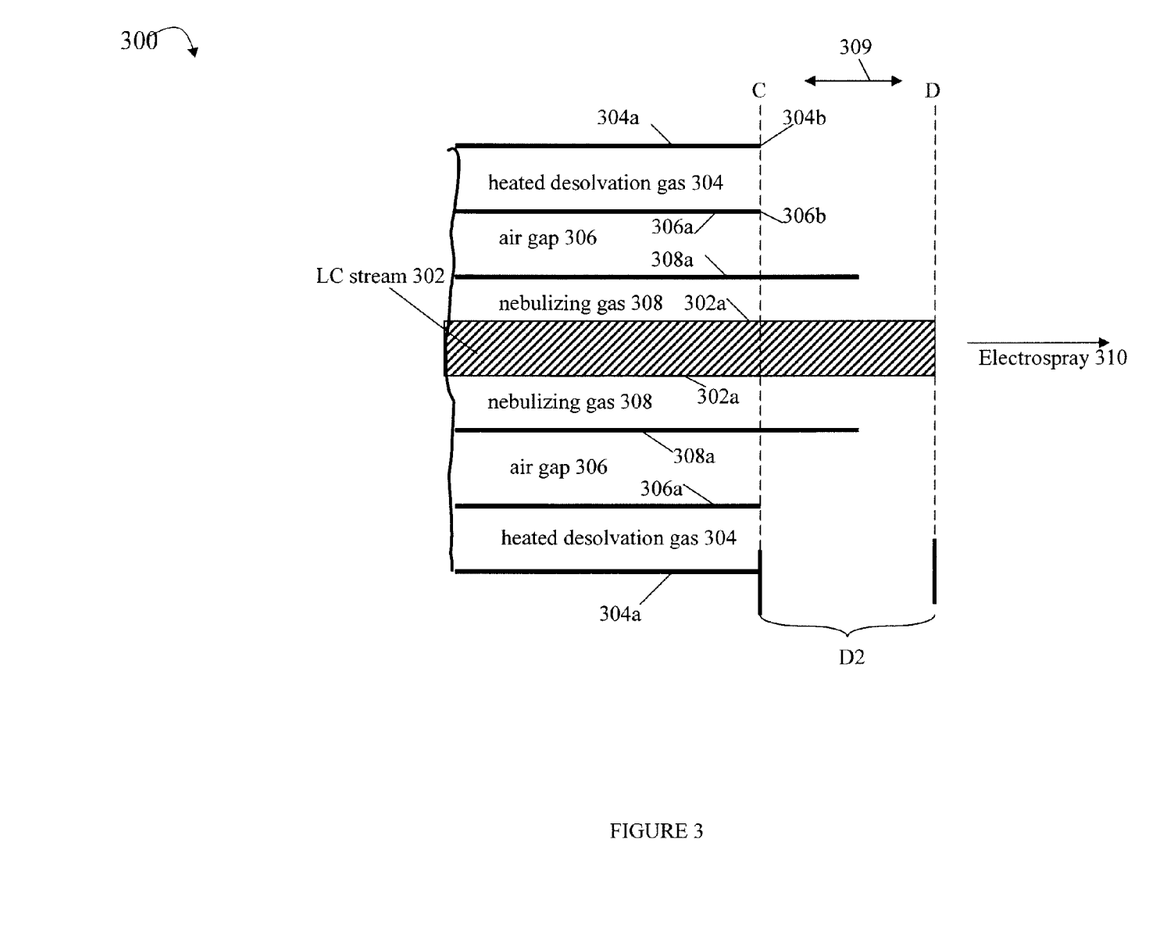
FIG. 3 is an example of a second tubing arrangement that may be used in an embodiment of the system of FIG. 1 in accordance with techniques herein.

Referring to FIG. 3, shown is an example of an enlarged lateral view of concentric tubes that may be used in an embodiment of FIG. 1 at the LC/MS interface where electrospray ionization occurs. The example 300 includes the concentric tubes as included in FIG. 2 and additionally includes further surrounding concentric tubes to facilitate use of a heated desolvation gas. An embodiment in accordance with techniques herein may use the tubing arrangement as illustrated in FIG. 3 replacing that as described in FIG. 2. As illustrated in 200, the example 300 includes the first inner tube 302a through which the LC stream flows and which is surrounded by a second concentric tube 308a through which the nebulizing gas flows. The example 300 further includes a third concentric tube 306a surrounding the second concentric tube and a fourth concentric tube 304a surrounding 306a. The heated desolvation gas 304 flows between the walls of the third 306a and fourth 304a concentric tubes in a manner similar to that of the nebulizing gas 308 (e.g., exiting the tubing at the end illustrated by C at the LC/MS interface where electrospray ionization occurs). The tubes 304a and 306a may end at approximately the same point C at the LC/MS interface where electrospray ionization occurs.

In an embodiment in accordance with techniques herein, another parameter that may be automatically adjusted using ion signal intensity feedback is the distance D2 which represents the relative distance between the end of the tubing 304a, 306a (e.g., position C), at which the heated desolvation gas exits and the end of the inner tube 302a (e.g., position D) at which the LC stream exits to form the electrospray 310. The distance D2 may be varied and adjusted in a manner similar to that as described herein with respect to D1. D2 may be varied by automatically adjusting the position of the tubes 304a and 306a (as represented by C) relative to tubes 308a and 302a (which may remain stationary). Using a motor and ion signal intensity feedback as described above, tubes 304a and 306a may be linearly adjusted in position along a two-dimensional axis as represented by 309 in a manner similar to that in which the tube 204a of FIG. 2 may be adjusted with respect to tube 202a. It will be appreciated by those skilled in the art that, although the distance D2 may be adjusted by having tubes 302a and 308a remain stationary and linearly adjusting tubes 304a and 306a as described above, the distance D2 may also be varied by having the tubes 304a and 306a remain stationary and linearly adjusting the position of tubes 302a and 308a (as a unit to maintain a constant distance D1), or adjusting the positions of 304a, 306a (e.g., as a unit so that the position of 304a and 306a relative to one another remains constant) and also 302a, 308a (as a unit so that the position of 302a and 308a relative to one another remains constant) to obtain a desired D2. Thus, adjustments to D2 may be automatically performed using the ion signal intensity feedback in accordance with techniques herein.

It should be noted that in an embodiment in accordance with techniques herein, tubes 304a and 306a may also not end at approximately the same point C. Rather, for example, the end 304b of tube 304a may extend beyond point C and the end 306b of tube 306a may end at point C. In this case, the relative distance between the end 304b of tube 304a and the end 306b of tube 306a may remain constant and may be positioned as a unit as described above when varying the distance D2.

It should be noted that the distance D2 may also be characterized as a relative distance between two exit points in a tubing arrangement of a plurality of concentric tubes, wherein a first of the two exit points is at a location where said liquid analyte stream exits the tubing arrangement, and a second of the two exit points is a location at which a heated desolvation gas exits the tubing arrangement.

Figure 4:
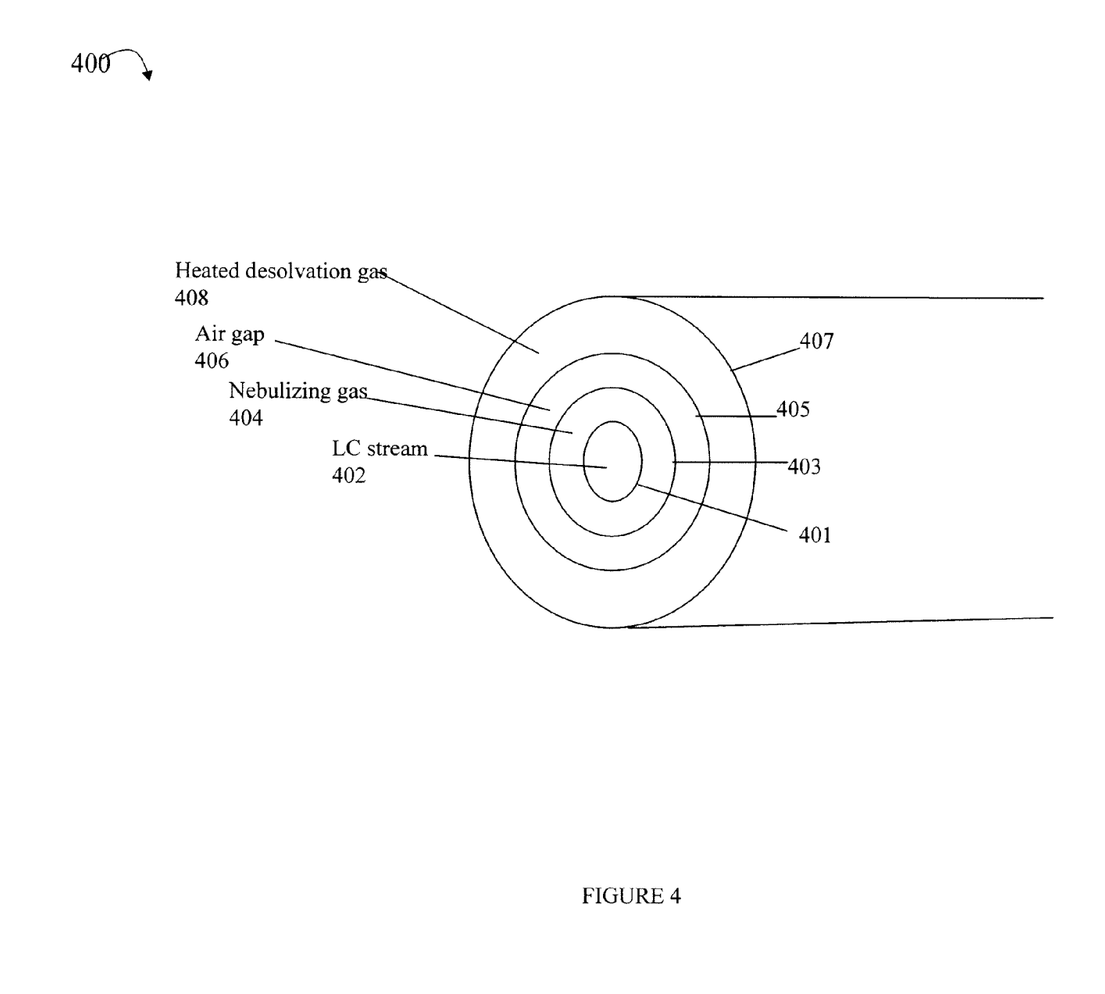
FIG. 4 illustrates an additional view of the tubing arrangement of FIG. 3.

Referring to FIG. 4, shown is another view of the plurality of concentric tubes of FIG. 3 that may be used in an embodiment in accordance with techniques herein. As described in connection with FIG. 3, the example 400 illustrates an LC stream 402 flowing through an innermost tube 401 and which is surrounded by a nebulizing gas 404 flowing in a second concentric tube 403. The nebulizing gas 404 (and second concentric tube) is surrounded by a third concentric tube 405 enclosing an air gap layer 406. The air gap layer 406 (and third concentric tube) is surrounded by a fourth concentric tube 407 through which a heated desolvation gas 408 flows.

The techniques herein may be used in connection with an embodiment using any suitable desolvation gas operating at a suitable temperature, pressure, flow rate, and the like, as may vary with other parameters and settings in each embodiment.

Figure 5:
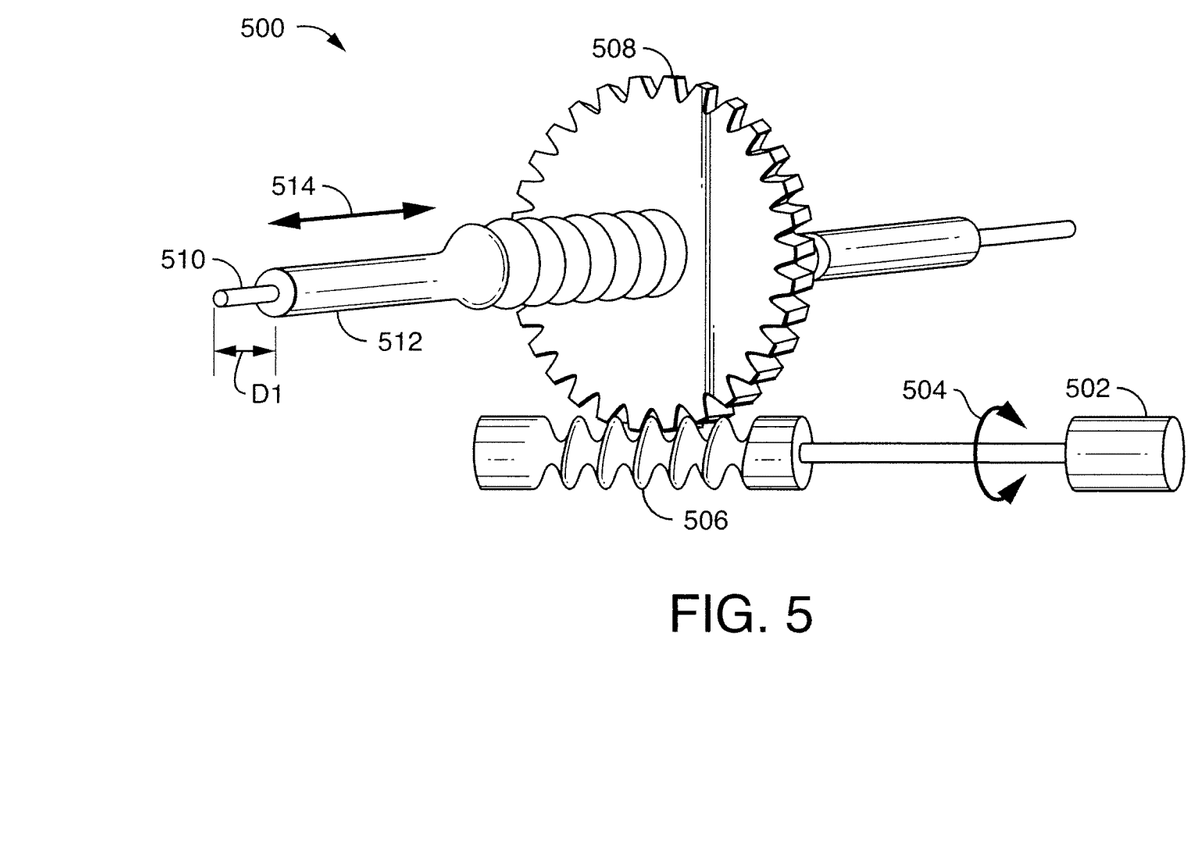
FIG. 5 is an example of an embodiment of components that may be used to adjust a nebulizing gas tube.

Referring to FIG. 5, shown is an illustration of components that may be used to position the nebulizing tube in an embodiment in accordance with techniques herein such as illustrated in FIG. 2. The example 500 illustrates an arrangement of components that may used to control positioning of the nebulizing gas tube (e.g., 204a of FIG. 2). However, as will be appreciated by those skilled in the art, other techniques may be used to control the positioning of the nebulizing gas tube relative to the concentric inner tube through which LC liquid stream (e.g., tube 202a of FIG. 2) flows. Additionally, the components of 500 may also adapted to vary and adjust the position of one or more other tubes as also described herein in connection with the distances D1 and/or D2.

The example 500 includes a worm gear 506, a motor 502, a drive gear 508, and a concentric nebulizing gas tube 512 surrounding an inner tube containing the LC stream 510. The tube 512 is threaded and may be positioned at various locations along the two-dimensional axis indicated by 514 as the drive gear 508 rotates about its center axis in a clockwise or counterclockwise direction. In operation, the motor 502 may receive control signals from the computer system causing the motor to rotate the worm gear 506 radially 504 about its center axis in a clockwise or counterclockwise direction. The worm gear 506 is coupled to the drive gear 508. The drive gear 508 rotates about its center axis in response to rotation of the worm gear 506. The drive gear 508 has the threaded tubing 512 passing through the center thereof so that as the drive gear 508 rotates, the tubing 512 has its position varied linearly along 514. An embodiment may use the foregoing arrangement to allow for fine adjustments to the distance D1. For example, appropriate gear ratios may be selected in accordance with a desired adjustment granularity such that multiple rotations of the worm gear cause a relatively small amount of rotation of the drive gear.

The example 500 of FIG. 5 illustrates components that may be included in a positioning device or apparatus to adjust the position of the nebulizing gas tube 512 relative to the LC stream tube 510. With reference back to FIG. 1, the computer system 102 may adjust the positioning of the tube 120 by determining whether the motor is to rotate the worm gear in the clockwise or counterclockwise direction and also determining a radial distance or amount by which the motor is to rotate the worm gear and thus causing the linear positioning 108a of the tube 120 to accordingly vary.

Although a particular arrangement to facilitate movement of one or more tubes is illustrated in FIG. 5, an embodiment may, more generally, use any suitable motor, gear arrangement, and the like.

Figure 6:
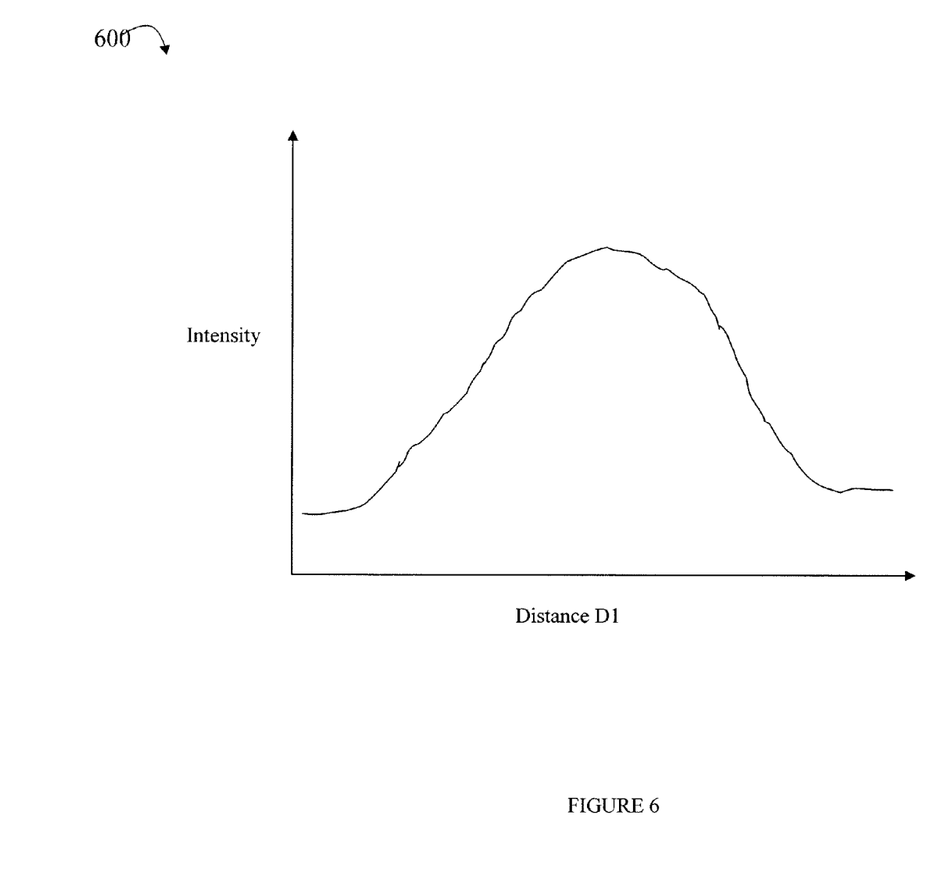
FIG. 6 is an example graphically illustrating how ion signal intensity may vary with respect to a distance D1 from the end of a tubing from which an LC stream exits to the end of another surrounding concentric tubing from which a nebulizing gas flows.

Referring to FIG. 6, shown is a graphical illustration approximating how ion signal intensity for an ion of interest may vary with the distance parameter D1. The example 600 generally illustrates that, for an optimal D1 resulting in a maximum or peak ion signal intensity, the ion signal intensity tends to decrease for D1 values greater than the optimal D1. Additionally, the ion signal intensity tends to decrease for D1 values less than the optimal D1. An embodiment may use the techniques herein with ion signal intensity feedback to discover the curve of the example 600 with particular intensity and corresponding D1 values for an ion of interest. The techniques herein may provide for automatically traversing a range of D1 values (and thus relative tubing positions) to select the D1 value (and associated tubing position) yielding the maximum ion signal intensity for an ion of interest.

With reference back to FIG. 1 in an embodiment operating in the first tuning mode, an infusion pump 131 may be used. It may be desirable to determine an optimal D1 value for analyzing an analyte of interest having a known m/z. As such, the ion signal intensity of the MS spectrum is monitored with respect the m/z for the ion or analyte of interest. The techniques herein may then be used to automatically traverse a range of values for D1 (e.g., with reference to FIG. 2 by adjusting the relative positions of tubes 204a and 202a) and examine the corresponding ion signal intensities in the MS spectra for the ion of interest. Based on the foregoing, the computer system may automatically select the optimal value for D1 yielding the maximum ion signal intensity. As described above, once the optimal value for D1 is determined so that D1 is tuned for the particular ion of interest, the infusion pump 131 may be replaced with a liquid chromatograph 130. The system may then perform analysis using the liquid chromatograph 130 with a fixed value of D1 equal to that as determined as optimal for the ion of interest (by operation of the system using the ion signal intensity feedback in the first tuning mode). In this manner, the system may be initially operating in the first mode to tune the parameter D1 and determine an optimal value for D1 for an ion of interest. Subsequently, the system may then operate to perform analysis for the ion of interest using the optimal value for D1 having a value selected to maximize ion signal intensity for the ion of interest. If analysis is then desired for a second ion of interest, the foregoing may be repeated to determine an optimal D1 value for the second ion of interest and then perform analysis for the second ion of interest using its optimal D1 value.

Figure 7:
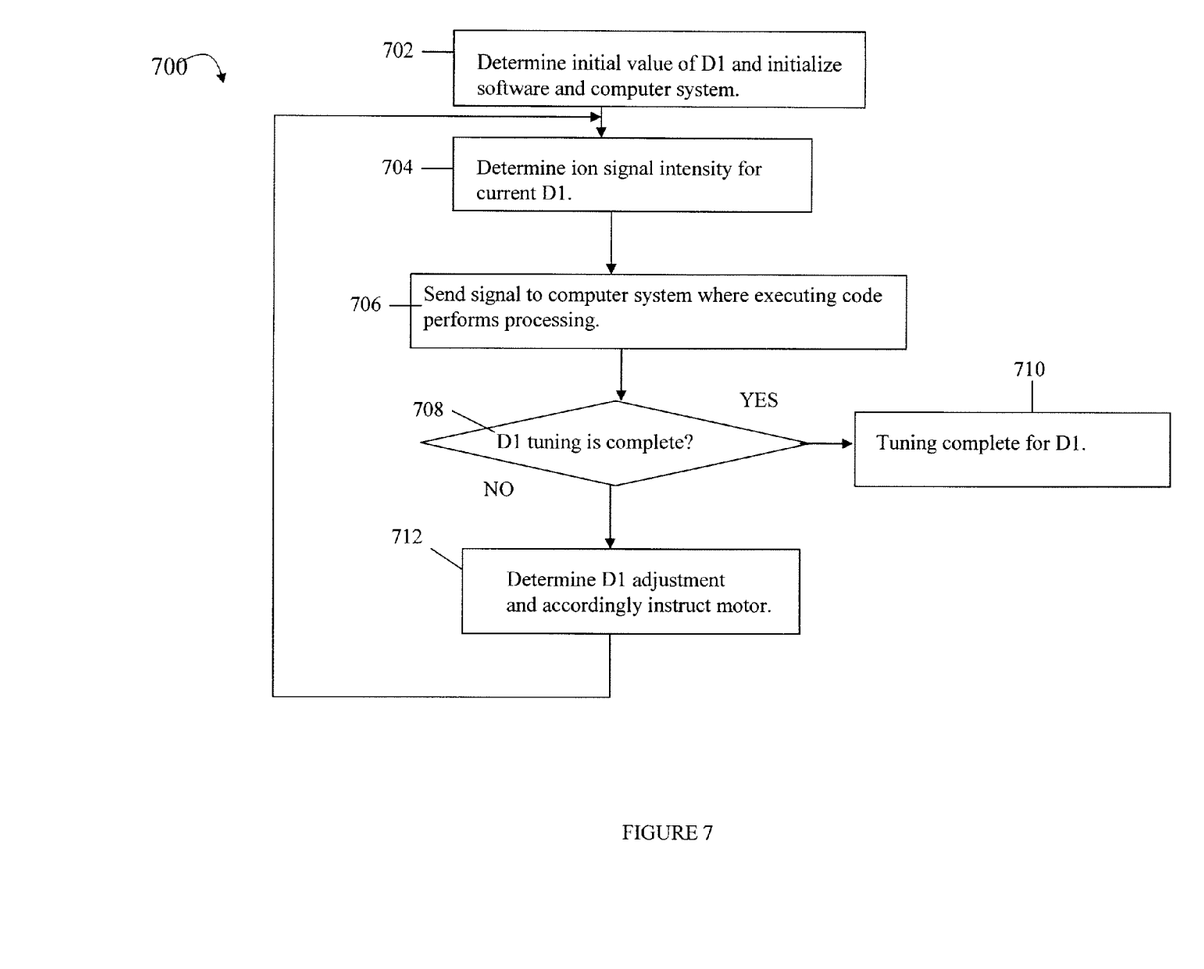
FIG. 7 is a flowchart of processing steps that may be performed in an embodiment in accordance with techniques described herein.

Referring to FIG. 7, shown is a flowchart of processing steps that may be performed in an embodiment in accordance with the techniques herein. The flowchart 700 summarizes processing as may be performed during operation of the embodiment of FIG. 1 described above when adjusting the position of the tubing 120 to vary the distance D1 and obtain a maximum ion signal intensity for a given ion of interest.

At step 702, an initial value for D1 is selected. Additionally, any initialization of the computer system, software, positioning of the tubing 120 to obtain the initial value of D1, and the like, for use with the automated techniques herein is performed. Code executing on the computer system may determine an initial position for the tubing 120 to obtain the initial value for D1 and accordingly instruct the motor. Step 702 may also include selecting a particular ion (and associated m/z of interest) to be observed and for which the ion signal intensity is measured in subsequent processing by the mass spectrometer. At step 704, the ion signal intensity of the ion of interest is measured for the current value of D1. At step 706, the ion signal intensity as determined by the mass spectrometer is transmitted to the computer system. The computer system may perform processing to determine, at step 708, whether any adjustment to D1 is needed, or more generally, whether tuning of parameter D1 is complete. Such a determination may be made, for example, by determining that the current value for D1 as obtained in step 704 results in a maximum ion signal intensity (or within an acceptable threshold). If step 708 evaluates to yes, the tuning of the parameter D1 is complete in that the techniques herein have been used to determine that the current value for D1 is optimal to obtain a maximum ion signal intensity for the particular ion of interest. If step 708 evaluates to no, control proceeds to step 712 where the computer system also determines an amount and type of adjustment to be made for D1. Step 712 also includes the computer system providing control signals to the motor to appropriately position the tubing 120 for any desired D1 adjustments. From step 712, control proceeds to step 704. As illustrated, steps 704, 706, 708 and 712 may be repeated until the value of D1 (as may be obtained by relative positioning and movement of tubing 120 of FIG. 1) results in obtaining a maximum ion signal intensity for a desired ion of interest. The steps of the flowchart 700 may be performed with respect to each ion of interest in order to tune the parameter D1 for each such ion.

For each iteration of flowchart 700, whether the current value of D1 is increased or decreased and by how much may vary with the particular tuning algorithm and technique used in an embodiment, previous adjustments to D1 and resulting ion signal intensities (from previous iterations of steps 704, 706, 708 and 712), and the like. For example, as described elsewhere herein, an embodiment may perform several iterations of steps 704, 706, 708 and 712 to traverse a range of D1 values and record the associated ion signal intensity for each such D1 value in the range. The computer system may then determine which of the D1 values yields the largest ion signal intensity and set D1 to be that particular value (and also accordingly instruct the motor to position the tube(s)). Thus, the feedback processing as described and illustrated in FIG. 7 may be used to discover the curve illustrated in FIG. 6 for an ion of interest and select an optimal D1 resulting in a maximum ion intensity. As an alternative, step 708 may determine that tuning of D1 is complete and the current D1 is to be used as the tuned value if the resulting ion signal intensity is within an acceptable threshold or limit. In this latter case, the acceptable ion signal intensity may not be the maximum intensity but may rather be a sufficient intensity within an acceptable intensity range, more than a specified threshold value, and the like.

It should also be noted that in the exemplary embodiment described above, a single computing device is illustrated as performing processing steps described. However, an embodiment may use one or more computing devices in connection with performing processing as described herein.

The steps of flowchart 700 are illustrated with respect to a particular parameter D1. However, the techniques and processing illustrated may be used in connection with tuning and selecting an optimal value for D2. Furthermore, more generally, the techniques of ion signal intensity feedback for automatically adjusting and determining parameter values for a particular ion may be used with tuning a variety of different parameters, also referred to as ion source parameters, in addition to D1 and D2. For example, the techniques herein for ion signal intensity feedback may be used to automatically tune and adjust one or more ion source parameters including distance D1, distance D2, the nebulizer gas pressure, nebulizer gas flow, desolvation gas temperature, desolvation gas flow, three-dimensional (XYZ) positioning of the electrospray interface with respect to the mass spectrometer, and the like. It should be noted that the electrospray interface is the interface at which electrospray ionization occurs. With reference to FIG. 1, the XYZ positioning may refer to three-dimensional orientation and placement of the tubing arrangement (e.g. tubes 115 and 120) with respect to the mass spectrometer inlet 107.

Any measurements, pressures, flow rates, voltages, and the like, provided herein are approximate and exemplary and should not be construed as a limitation of the techniques herein which, as will be appreciated by those skilled in the art, may more generally be used in an embodiment with any suitable values.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. A system comprising:
   a tubing arrangement including a first tube surrounded by a second tube, wherein an analyte stream flows through said first tube and exits at a first end thereof, said second tube having a nebulizing gas flowing therethrough that exits said second tube at a second end thereof, wherein at least said second tube is linearly movable with respect to a center axis therethrough;
   a positioning apparatus configured to linearly adjust a position of said second end of said second tube relative to said first end of said first tube in response to control signals;
   a mass spectrometer configured to output a signal indicating an ion signal intensity for an ion; and
   a computing device electrically connected to said mass spectrometer and said positioning apparatus, said computing device configured to receive said signal from said mass spectrometer indicating said ion signal intensity for the ion, to determine, in accordance with said signal, an adjustment to a current position of said second end of said second tube relative to said first end of said first tube, and to send said control signals to the positioning apparatus to linearly adjust a current position of the second tube relative to the first tube in accordance with the adjustment.

2. The system of claim 1, wherein said computing device is further configured to repeatedly determine an adjustment to a current position of said second end of said second tube relative to said first end of said first tube, and accordingly send control signals to said positioning apparatus until said ion signal intensity of the ion is determined as acceptable by said computing device.

3. The system of claim 2, wherein said ion signal intensity is determined as acceptable if said ion signal intensity is a maximum ion signal intensity for the ion.

4. The system of claim 2, wherein said ion signal intensity is determined as acceptable when more than a specified threshold intensity.

5. The system of claim 1, wherein said positioning apparatus includes a motor, a worm gear and a drive gear, said motor being coupled to said worm gear, said worm gear being coupled to said drive gear, and wherein said motor receives control signals from the computing device causing said worm gear to rotate about its center axis, and said drive gear rotates about its center axis in response to rotation of said worm gear about its center axis.

6. The system of claim 5, wherein said second tube is threaded and passes through a center of said drive gear and, in response to the drive gear rotating about its center axis, the second tube has its position varied linearly.

7. The system of claim 1, further comprising one of a pump or a liquid chromatograph coupled to the tubing arrangement and providing the analyte stream.

8. The system of claim 6, wherein said computing device determines an amount by which said motor is to rotate the worm gear.

9. A method for tuning parameters of a system comprising:
performing, for each value in a set of one or more values of a distance, mass spectral analysis of a liquid analyte stream when said distance is set to said each value and obtaining a corresponding ion signal intensity of a selected ion, wherein said distance is measured from a first end of a first tube to a second end of a second tube which surrounds said first tube, said liquid analyte stream flowing through said first tube and exiting at said first end, a nebulizing gas flowing through said second tube and exiting at said second end;
automatically adjusting, using a computing device, a current value of said distance in accordance with one or more corresponding ion signal intensities obtained for said selected ion by performing said mass spectral analysis; and
automatically determining, using a computing device, a desired value for said distance using corresponding ion signal intensities of said selected ion obtained from performing said mass spectral analysis, wherein said desired value for said distance results in an ion signal intensity for said selected ion which is any of more than a threshold intensity and a maximum of a plurality of ion signal intensities obtained by performing said mass spectral analysis using different values for said distance.

10. The method of claim 9, wherein said distance is adjusted by adjusting a position of one or more of said first tube and said second tube using a positioning apparatus controlled by a computing device.

11. The method of claim 10, wherein said positioning apparatus includes a motor which operates responsive to control signals transmitted by a computing device.

12. A method for tuning parameters of a system comprising:
performing, for each value in a set of one or more values of a distance, mass spectral analysis of a liquid analyte stream when said distance is set to said each value and obtaining a corresponding ion signal intensity of a selected ion, wherein said distance is a relative distance between two exit points in a tubing arrangement of a plurality of concentric tubes, said first exit point being a location at which said liquid analyte stream exits said tubing arrangement, said second exit point being a location at which a heated desolvation gas exits said tubing arrangement;
automatically adjusting, using a computing device, a current value of said distance in accordance with one or more corresponding ion signal intensities obtained for said selected ion by performing said mass spectral analysis; and
automatically determining, using a computing device, a desired value for said distance using corresponding ion signal intensities of said selected ion obtained from performing said mass spectral analysis, wherein said desired value for said distance results in an ion signal intensity for said selected ion which is any of more than a threshold intensity and a maximum of a plurality of ion signal intensities obtained by performing said mass spectral analysis using different values for said distance.

13. The method of claim 12, wherein said tubing arrangement includes a first tube through which said liquid analyte stream flows and which is surrounded by a second tube through which a nebulizing gas flows, said second tube being surrounded by a third tube enclosing an air gap, said third tube being surrounded by a fourth tube, said heated desolvation gas flowing between said third tube and said fourth tube.

14. The method of claim 13, wherein said distance is adjusted by adjusting a position of one or more of said first tube, and said third and fourth tubes using a positioning apparatus controlled by a computing device.

15. The method of claim 14, wherein said positioning apparatus includes a motor which operates responsive to control signals transmitted by a computing device.

16. A method for tuning one or more ion source parameters comprising:
selecting an ion; and
for each of said one or more ion source parameters, performing processing including:
performing, for each value in a set of one or more values for said each ion source parameter, mass spectral analysis of a liquid analyte stream when said each ion source parameter is set to said each value and obtaining a corresponding ion signal intensity of said ion;
automatically adjusting, using a computing device, a current value of said each ion source parameter in accordance with one or more corresponding ion signal intensities for said ion obtained by performing said mass spectral analysis; and
automatically determining, using a computing device, a desired value for said each ion source parameter using corresponding ion signal intensities obtained from performing said mass spectral analysis of said ion, wherein said desired value for said each ion source parameter results in an ion signal intensity for said ion which is any of more than a threshold intensity and a maximum of a plurality of ion signal intensities obtained by performing said mass spectral analysis using different values for said each ion source parameter, said one or more ion source parameters including at least one of a first distance measured from a first end of a first tube through which a liquid analyte stream flows and exits at said first end to a second end of a second tube which surrounds said first tube and through which a nebulizing gas flows and exits at said second end, a second distance measured from said first end and a third end of a third tube from which a heated desolvation gas flows, a nebulizer gas pressure, a nebulizer gas flow, a desolvation gas temperature, a desolvation gas flow, and a three-dimensional positioning of an electrospray interface with respect to a mass spectrometer performing the mass spectral analysis, said electrospray interface being an interface at which electrospray ionization occurs.

17. The method of claim 16, wherein said liquid analyte stream is injected using an infusion pump when tuning each of said one or more ion source parameters.

18. The method of claim 17, wherein once a desired value for each of said one or more ion source parameters is determined, the infusion pump is replaced with a liquid chromatograph.

19. The method of claim 18, wherein once a desired value for a first of said one or more ion source parameters is determined, the first ion source parameter is set to said desired value when performing subsequent analysis.

* * * * *